US012805864B2

(12) United States Patent
Liu

(10) Patent No.: US 12,805,864 B2
(45) Date of Patent: Nov. 24, 2026

(54) SURGICAL FASTENER APPLYING APPARATUS WITH LOCKOUT ASSEMBLY

(71) Applicant: Covidien LP, Mansfield, MA (US)

(72) Inventor: Chirong Liu, Shanghai (CN)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 19/237,833

(22) Filed: Jun. 13, 2025

(65) Prior Publication Data

US 2025/0366851 A1 Dec. 4, 2025

Related U.S. Application Data

(63) Continuation of application No. 18/025,753, filed as application No. PCT/CN2020/115839 on Sep. 17, 2020, now Pat. No. 12,349,900.

(51) Int. Cl.
*A61B 17/068* (2006.01)

(52) U.S. Cl.
CPC .................................. *A61B 17/068* (2013.01)

(58) Field of Classification Search
CPC .................................................... A61B 17/068
See application file for complete search history.

(56) References Cited

U.S. PATENT DOCUMENTS 6,131,789 A 10/2000 Schulze et al.
7,631,794 B2 12/2009 Rethy et al.
10,512,461 B2 12/2019 Gupta et al.
2012/0312861 A1 12/2012 Gurumurthy et al.
2013/0037594 A1 2/2013 Dhakad et al.
2017/0143335 A1* 5/2017 Gupta .............. A61B 17/07207
2023/0346370 A1 11/2023 Liu

FOREIGN PATENT DOCUMENTS

CN 101507629 B 11/2012
CN 105682569 A 6/2016
CN 103732156 B 4/2017
CN 210811266 U 6/2020

OTHER PUBLICATIONS

International Search Report for Application No. PCT/CN2020/115839 dated Jun. 16, 2021, 6 pages.
Written Opinion for Application No. PCT/CN2020/115839 dated Jun. 16, 2021, 4 pages.

* cited by examiner

*Primary Examiner* — Michelle Lopez

(57) ABSTRACT

The surgical fastener applying apparatus includes an anvil half-section, a cartridge receiving half-section, a firing assembly including a push plate, and a lockout assembly. The cartridge receiving half-section defines an elongated channel member. The elongated channel member is configured to receive a single use loading unit (SULU). The lockout assembly is supported in the elongated channel member and includes a lockout that is selectively engageable with the push plate to prevent movement of the push plate relative to the lockout when the SULU is not supported in the elongated channel member.

19 Claims, 7 Drawing Sheets

SURGICAL FASTENER APPLYING APPARATUS WITH LOCKOUT ASSEMBLY

CROSS-REFERENCE TO RELATED APPLICATIONS

This application is a continuation of U.S. patent application Ser. No. 18/025,753, filed Mar. 10, 2023, now U.S. Pat. No. 12,349,900, which is a National Stage Application of PCT/CN2020/115839, filed Sep. 17, 2020, the entire disclosure of each of which being incorporated by reference herein.

TECHNICAL FIELD

This disclosure relates to a surgical fastener applying apparatus and, more particularly, to a surgical fastener applying apparatus having reusable and disposable components.

BACKGROUND

Surgical fastener applying apparatus, wherein tissue is first grasped or clamped between opposing jaw structures and then joined by means of surgical fasteners, are well known in the art. In some such apparatus, a knife is provided to cut the tissue which has been joined by the fasteners. The fasteners are typically in the form of surgical staples, although, other surgical fasteners may also be utilized, such as, for example, clips or two-part polymeric surgical fasteners.

Surgical fastener applying apparatus typically include two elongated beam members which are used to capture or clamp tissue therebetween. Typically, one of the beam members carries a disposable cartridge assembly which houses a plurality of staples arranged in at least two lateral rows, while the other beam member includes an anvil which defines a surface for forming the staple legs as the staples are driven from the cartridge assembly. Where two-part fasteners are used, the beam member which includes the anvil carries a mating part of the two-part fastener, e.g. the receiver. Generally, the staple formation process is affected by the interaction between one or more longitudinally moving camming members and a series of individual staple pushers. As the camming members travel longitudinally through the cartridge carrying beam member, the individual pusher members are biased upwardly into a backspan of the staples supported within the cartridge assembly to sequentially eject the staples from the cartridge. A knife may be provided to travel with the camming members between the staple rows to cut the tissue between the rows of formed staples. An example of such an instrument is disclosed in U.S. Pat. No. 7,631,794, which is incorporated herein in its entirety by reference.

SUMMARY

According to one aspect of this disclosure, a surgical fastener applying apparatus includes an anvil half-section, a cartridge receiving half-section defining an elongated channel member, a firing assembly including a push plate, and a lockout assembly. The elongated channel member is configured to receive a single use loading unit (SULU). The lockout assembly is supported in the elongated channel member and includes a lockout that is selectively engageable with the push plate to prevent movement of the push plate relative to the lockout when the SULU is not supported in the elongated channel member.

In aspects, the lockout may be pivotally coupled to walls of the elongated channel member. The lockout may be movable between a locked position and an unlocked position. In the locked position, the lockout may prevent the push plate from distally translating through the lockout. The lockout may define a push plate passage therethrough. The push plate passage may be disposed in registration with the push plate. The push plate may define a lockout recess and the lockout may include a proximal tooth that is selectively receivable within the lockout recess. When the proximal tooth is received within the lockout recess, the proximal tooth prevents the push plate from advancing through the push plate passage.

In aspects, the lockout assembly may include a spring that urges the lockout into the locked position when the SULU is not disposed in the elongated channel member. The lockout may include arms that engage a stopper extending from the elongated channel member. The stopper may be configured to limit pivotal rotation of the lockout in a clockwise direction.

In aspects, the lockout assembly may prevent distal translation of the push plate. The lockout assembly may vertically constrain the push plate.

According to another aspect, a surgical fastener applying apparatus includes an anvil half-section, a cartridge receiving half-section defining an elongated channel member, a push plate, and a lockout. The elongated channel member is configured to receive a single use loading unit (SULU). The lockout is selectively engageable with the push plate. The push plate is vertically and horizontally constrained when the lockout is engaged with the push plate to prevent a firing of the surgical fastener applying apparatus when the SULU is not supported in the elongated channel member.

According to yet another aspect, a surgical fastener applying apparatus includes an anvil half-section, a cartridge receiving half-section defining an elongated channel member, a firing assembly including a push plate, and a lockout assembly. The elongated channel member is configured to receive a single use loading unit (SULU). The lockout assembly is supported in the elongated channel member and includes a lockout that is movable between a first position and a second position to selectively obstruct the push plate of the firing assembly when the SULU is not supported in the elongated channel member.

In aspect, in the first position, a tooth of the lockout may be received within a lockout recess of the push plate to limit horizontal and vertical movement of the push plate. In the second position, the push plate may be configured to distally advance through a push plate passage defined through the lockout.

The details of one or more aspects of this disclosure are set forth in the accompanying drawings and the description below. Other aspects, features, and advantages will be apparent from the description, the drawings, and the claims that follow.

BRIEF DESCRIPTION OF THE DRAWINGS

The accompanying drawings, which are incorporated in and constitute a part of this specification, illustrate embodiments of the disclosure and, together with the detailed description of the embodiments given below, serve to explain the principles of the disclosure.

DETAILED DESCRIPTION

Figure 1:
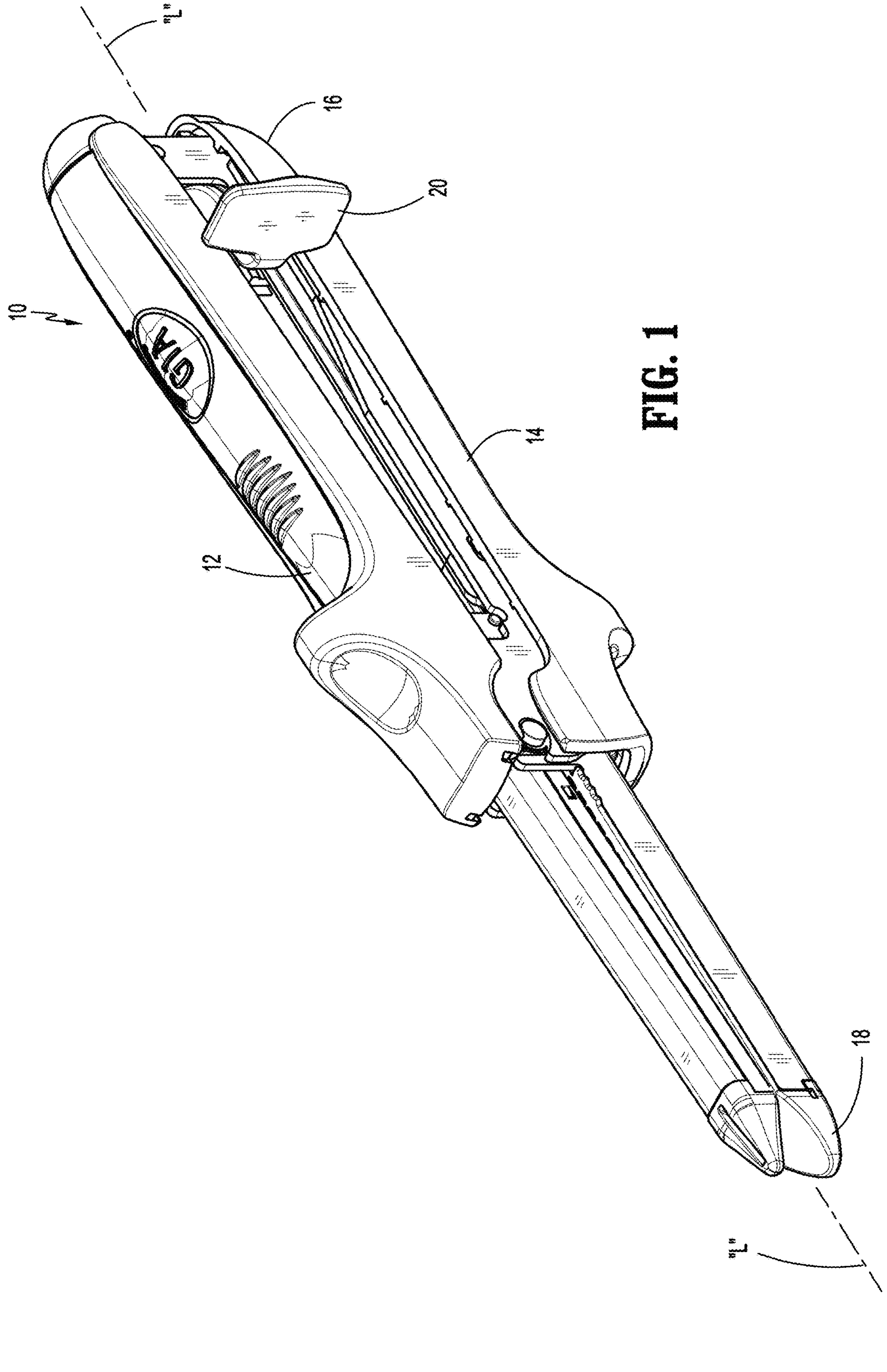
FIG. 1 is a perspective view of a surgical fastener applying apparatus in accordance with the principles of this disclosure.

Aspects of this disclosure are described in detail with reference to the drawings, in which like reference numerals designate identical or corresponding elements in each of the several views. Additionally, the term “proximal” or “trailing” refers to the portion of structure that is closer to the clinician and the term “distal” or “leading” refers to the portion of structure that is farther from the clinician. As commonly known, the term “clinician” refers to a doctor (e.g., a surgeon), a nurse, or any other care provider and may include support personnel.

In the following description, well-known functions or constructions are not described in detail to avoid obscuring this disclosure in unnecessary detail.

Figure 2:
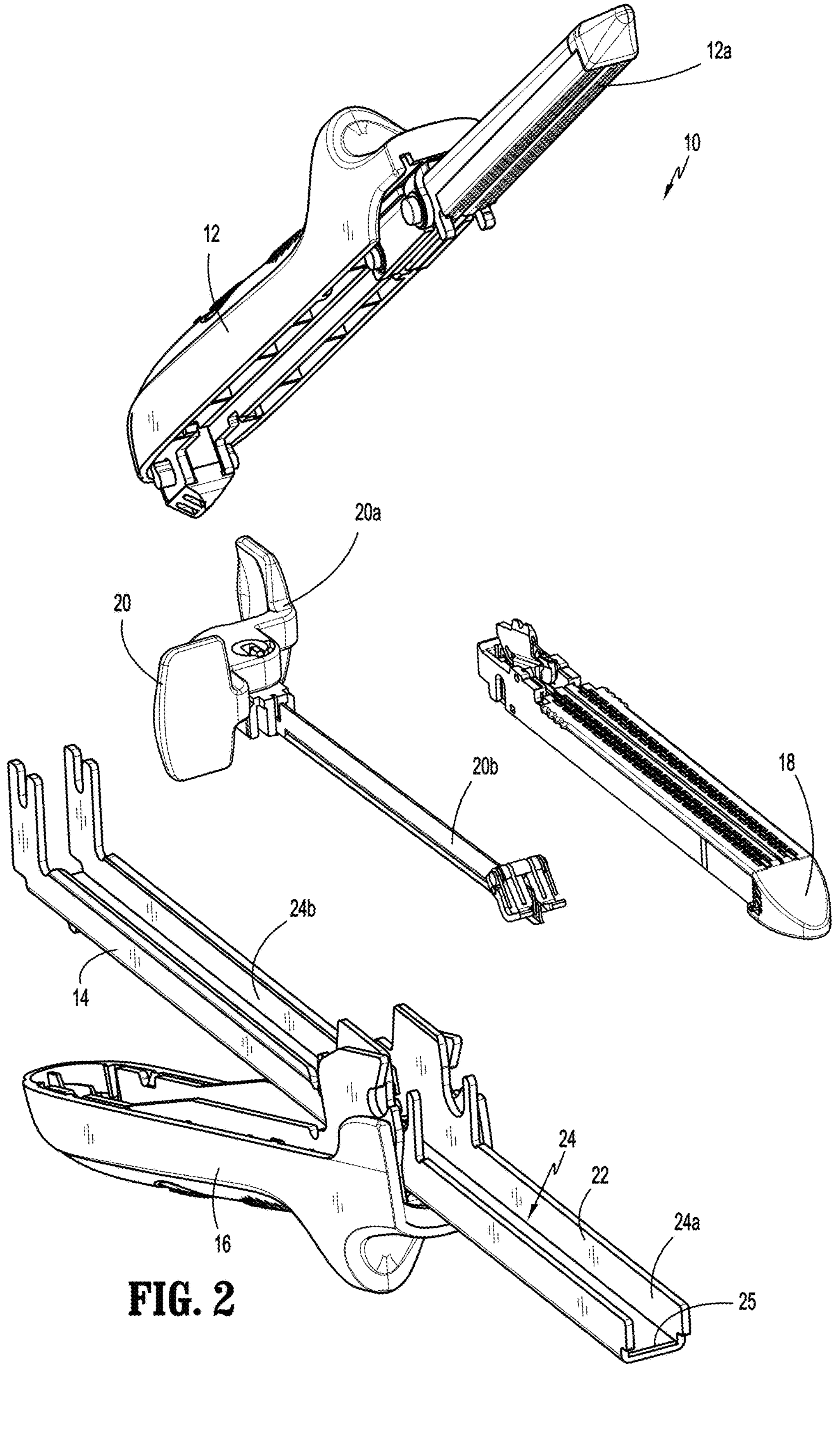
FIG. 2 is a perspective view, with parts separated, of the surgical fastener applying apparatus of FIG. 1.
Figure 4:
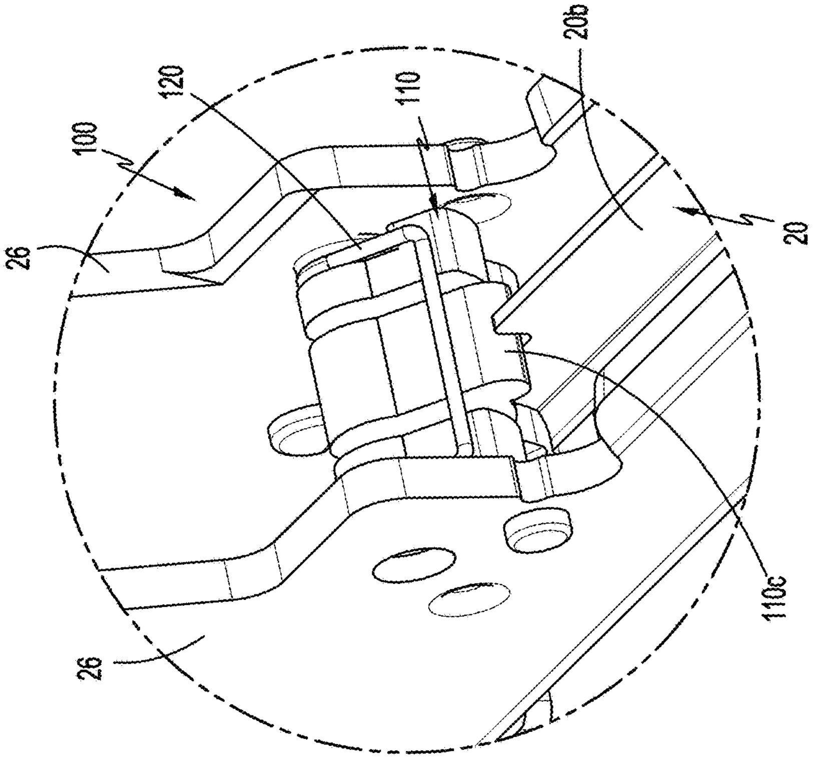
FIG. 4 is an enlarged, perspective view of the indicated area of detail shown in FIG. 3.
Figure 3:
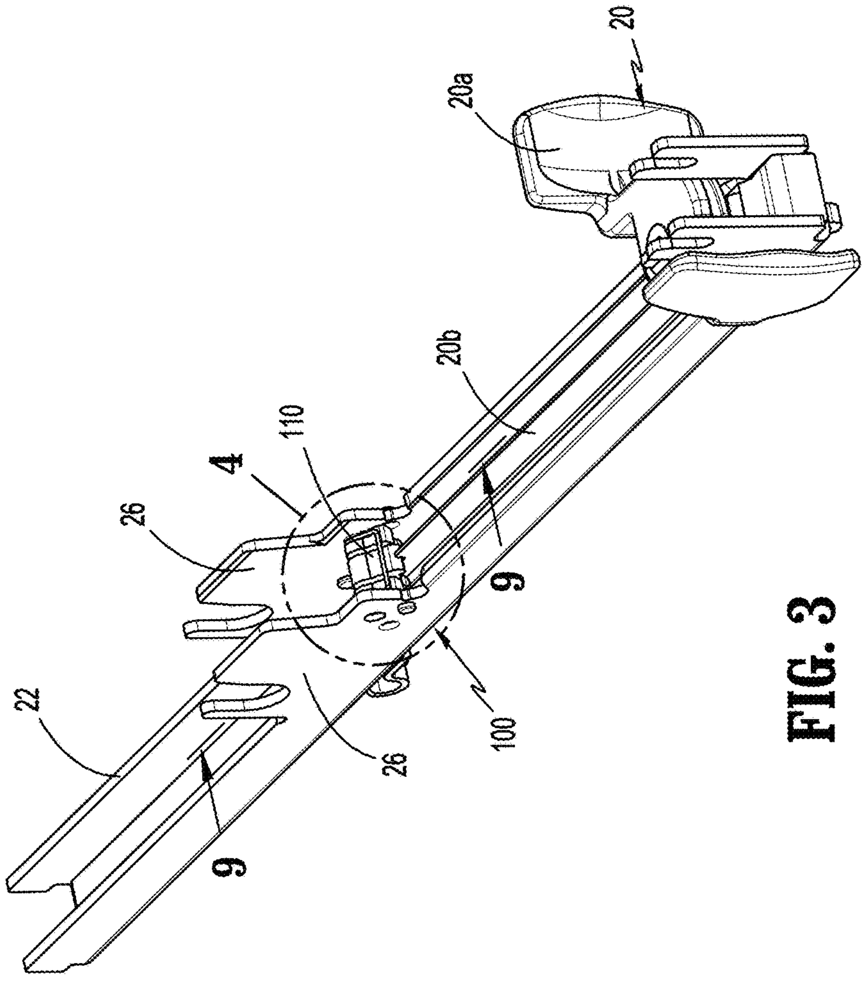
FIG. 3 is a perspective view of a portion of the surgical fastener applying apparatus of FIG. 1 with a lockout assembly thereof shown in a locked position.

Referring to FIGS. 1-12, and as best seen in FIGS. 1 and 2, surgical stapler or surgical fastener applying apparatus 10 defines a longitudinal axis “L” and includes an anvil half-section 12 having an anvil 12*a*, a cartridge receiving half-section 14, a clamping lever 16, a single use loading unit 18 (hereinafter “SULU”), a firing assembly 20, and a lockout assembly 100 having a lockout 110 and spring 120 (e.g., a torsion spring). Lockout assembly 100 prevents surgical stapler 10 from firing when SULU 18 is not loaded into cartridge receiving half-section 14. In aspects, anvil half-section 12, cartridge receiving half-section 14 and clamping lever 16 are constructed to be reusable components and, as such, are constructed from a biocompatible material suitable for sterilization and repeated use, e.g., stainless steel. In contrast, SULU 18 and firing assembly 20 are constructed to be disposable and, as such, may be constructed from any suitable biocompatible material, e.g., plastics, metals, combinations thereof, having the requisite strength characteristics. For a more detailed description of similar surgical staplers, one or more components of which can be included in surgical stapler 10, or modified for use with surgical stapler 10, reference can be made to U.S. Pat. Nos. 10,512,461 and 7,631,794, the entire contents of each of which are incorporated herein by reference.

Figure 7:
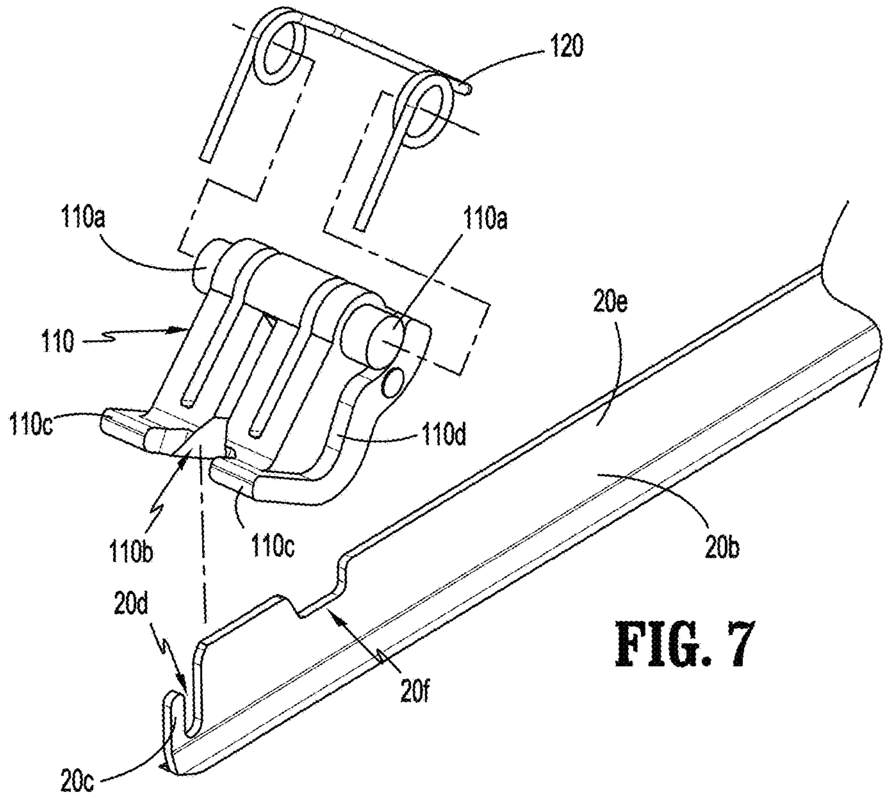
FIG. 7 is an enlarged, perspective view, with parts separated, of the lockout of FIG. 5 and a distal portion of a push plate of the firing assembly of FIG. 5.
Figure 8:
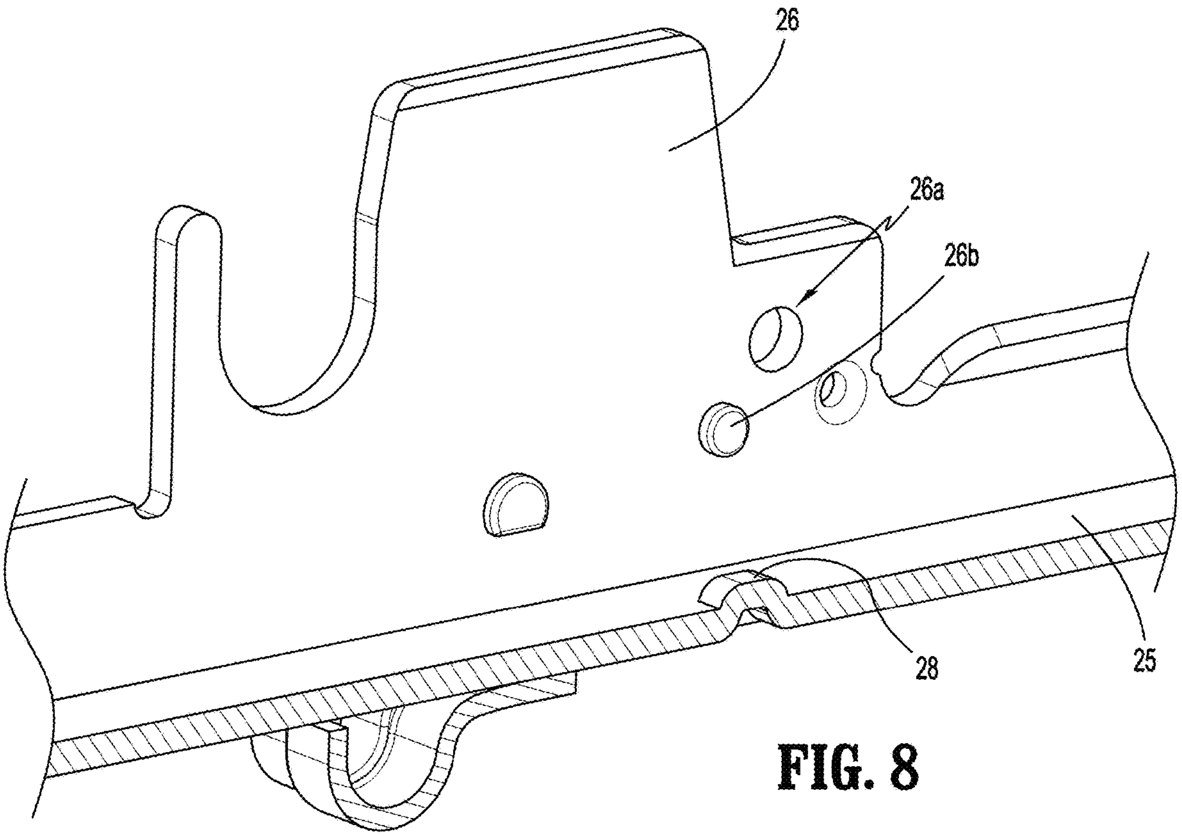
FIG. 8 is an enlarged, cross-sectional view of the elongated channel member of FIG. 5 as taken along section line 8-8 of FIG. 5.
Figure 9:
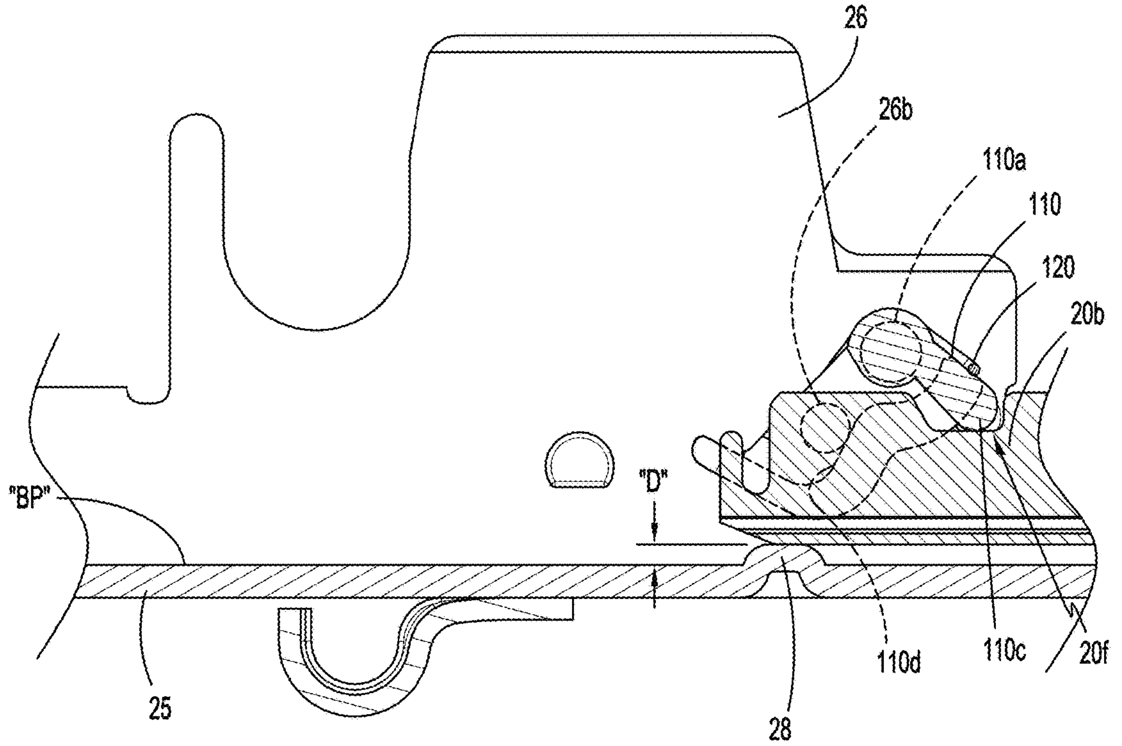
FIGS. 9-12 are progressive views illustrating a single use loading unit being secured to the elongated channel member and positioning the lockout assembly in an unlocked position.
Figure 10:
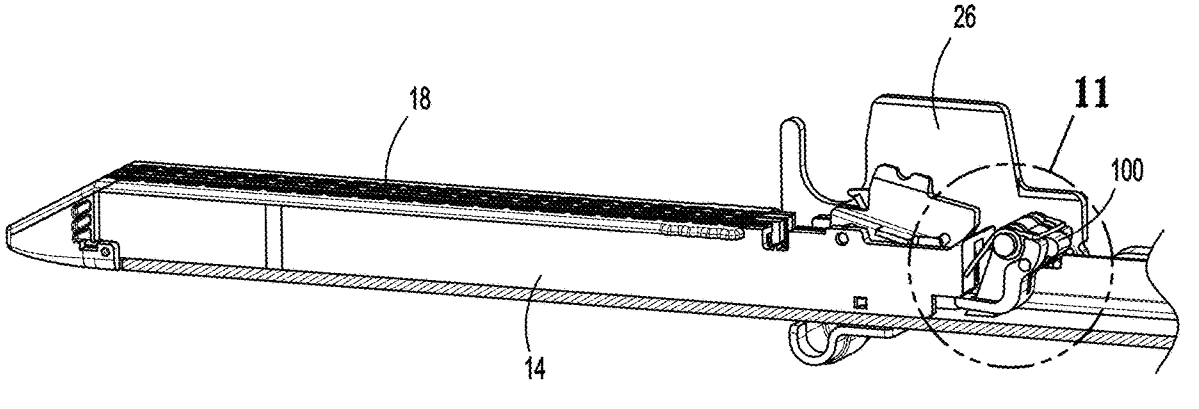

With brief reference to FIG. 7, firing assembly 20 includes a firing lever assembly 20*a* having a push plate 20*b* that extends distally from firing lever assembly 20*a*. Push plate 20*b* extends distally to a distal finger 20*c* and defines a finger recess 20*d* proximal to distal finger 20*c*. Push plate 20*b* further includes an elongate ridge 20*e* along a top surface thereof. Elongate ridge 20*e* defines a lockout recess 20*f* therein.

Figure 5:
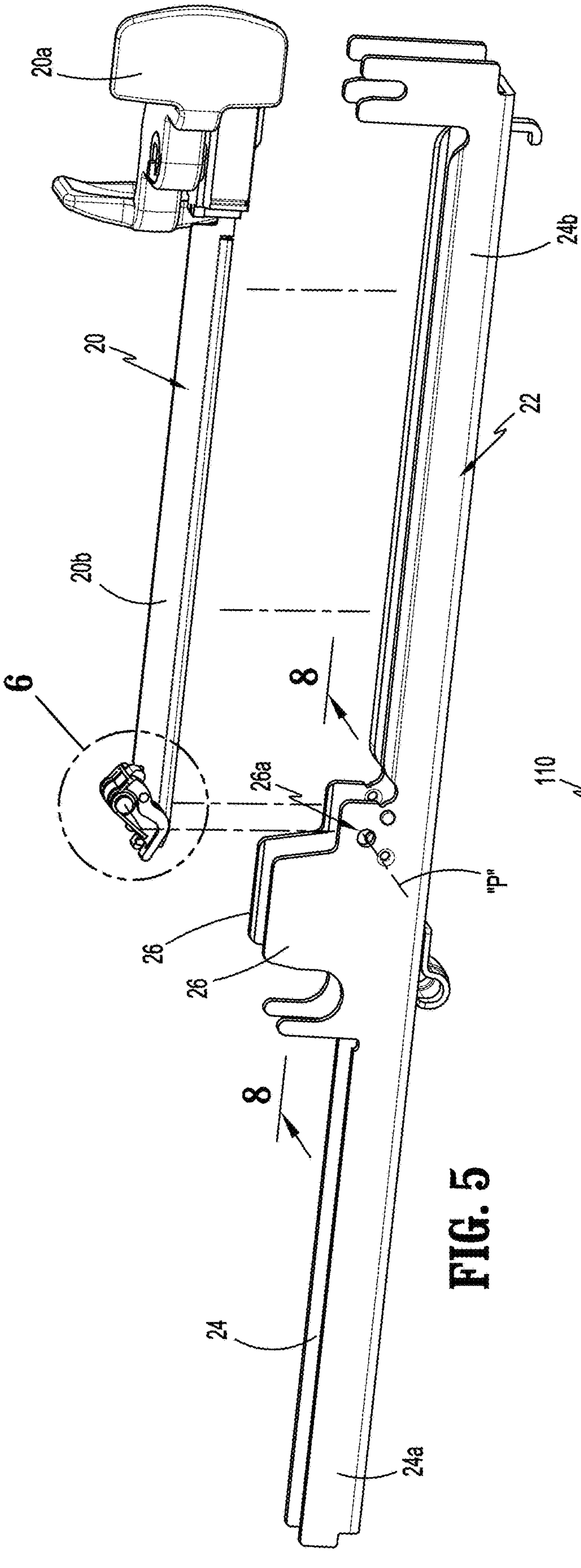
FIG. 5 is a side, perspective view, with parts separated, of an elongated channel member and a firing assembly of the surgical fastener applying apparatus of FIG. 1, the firing assembly shown with a lockout of the lockout assembly of FIG. 3 supported thereon.
Figure 6:
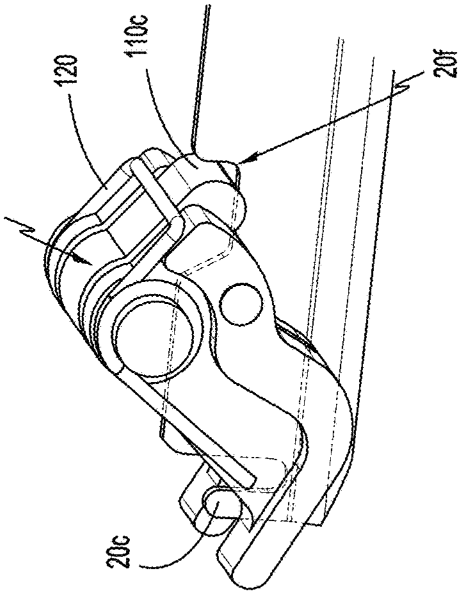
FIG. 6 is an enlarged view of the indicated area of detail shown in FIG. 5.

Referring to FIGS. 2, 5 and 7, cartridge receiving half-section 14 defines an elongated channel member 22 which defines a U-shaped channel 24 having a distal portion 24*a* configured to releasably receive SULU 18 and a proximal portion 24*b* configured to releasably receive firing assembly 20 therein. In general, when SULU 18 is supported in cartridge receiving half-section 14, anvil 12*a* and SULU 18 can be clamped together about tissue so that firing assembly 20 can be actuated to fire staples from SULU 18 and formed against anvil 12*a* for securing the staples to the tissue. Elongated channel member 22 has base 25 and upright walls 26 that extend from base 25 on opposite sides thereof to support lockout assembly 100 in elongated channel member 22. Upright walls 26 define support apertures 26*a* therethrough that enable lockout 110 to pivotably couple to upright walls 26 so that lockout 110 can pivot about pivot axis “P” (FIG. 5). Pivot axis “P” is transverse to longitudinal axis “L” (see FIG. 1). Upright walls 26 enable lockout 110 to selectively pivot between a first position engaged with push plate 20*a* of firing assembly 20 (e.g., a locked position) to prevent push plate 20*a* from advancing through lockout 110, and a second position disengaged from push plate 20*a* (e.g., an unlocked position) so that push plate 20*a* can advance through lockout 110. Elongated channel member 22 further includes a guide nub 28 that extends upwardly from base 25 to guide push plate 20*a* over base 25 at a predetermined distance “D” (FIG. 9) above a base plane “BP” of base 25 as push plate 20*a* slides along guide nub 28 when lockout 100 is disposed in the unlocked position. Each upright wall 26 further includes a stopper 26*b* (FIG. 8) that projects inwardly for selective engagement with lockout 110 when lockout 100 is disposed in the locked position.

With reference to FIG. 3-12, lockout 110 and spring 120 of lockout assembly 100 are coupled together to enable lockout 110 prevent surgical stapler 10 from firing when SULU 18 is not loaded into elongated channel member 22 of cartridge receiving half-section 14. Lockout 110 includes shoulders 110*a* that secure spring 120 to lockout 110 and which maintain lockout 110 pivotally coupled support apertures 26*a* of elongated channel member 22. Lockout 110 further includes a proximal tooth 110*c* that is selectively receivable within lockout recess 20*f* of push plate 20*b* of firing assembly 20 via spring force from spring 120 to inhibit distal movement of push plate 20*b* relative to lockout 110 when lockout assembly 100 is disposed in the locked position thereof. Lockout 110 defines a push plate passage 110*b* therethrough (e.g., centrally disposed) for receiving push plate 20*b* through lockout 110 when lockout assembly 100 is disposed in the unlocked position thereof. Lockout 110 also includes arms 110*d* that extend from opposite side surfaces of lockout 110 for selective engagement with stoppers 26*b* of upright walls 26 when lockout assembly 100 is disposed in the locked position thereof (see FIG. 9). Lockout 110 also include distal toes 110*e* that connect with distal portions of arms 110*d* at a distal end portion of lockout 110.

Turning now to FIGS. 9-12, when SULU 18 is not received within elongated channel member 22 of cartridge receiving half-section 14, spring 120 of lockout assembly

100 urges lockout 110 into the locked position (FIG. 9) so that proximal tooth 110*c* of lockout 110 is received within lockout recess 20*f* of push plate 20*b* and arms 110*d* of lockout 110 are engage with stoppers 26*b* of elongated channel member 22. In the locked position, with proximal tooth 110*c* in lockout recess 20*f*, proximal tooth 110*c* obstructs translation of push plate 20*b* relative to lockout 110 (e.g., horizontally constrained). Push plate 20*b* is also vertically constrained between guide nub 28 of elongated channel member 22 and proximal tooth 110*c* of lockout 110 in the locked position.

Figure 11:
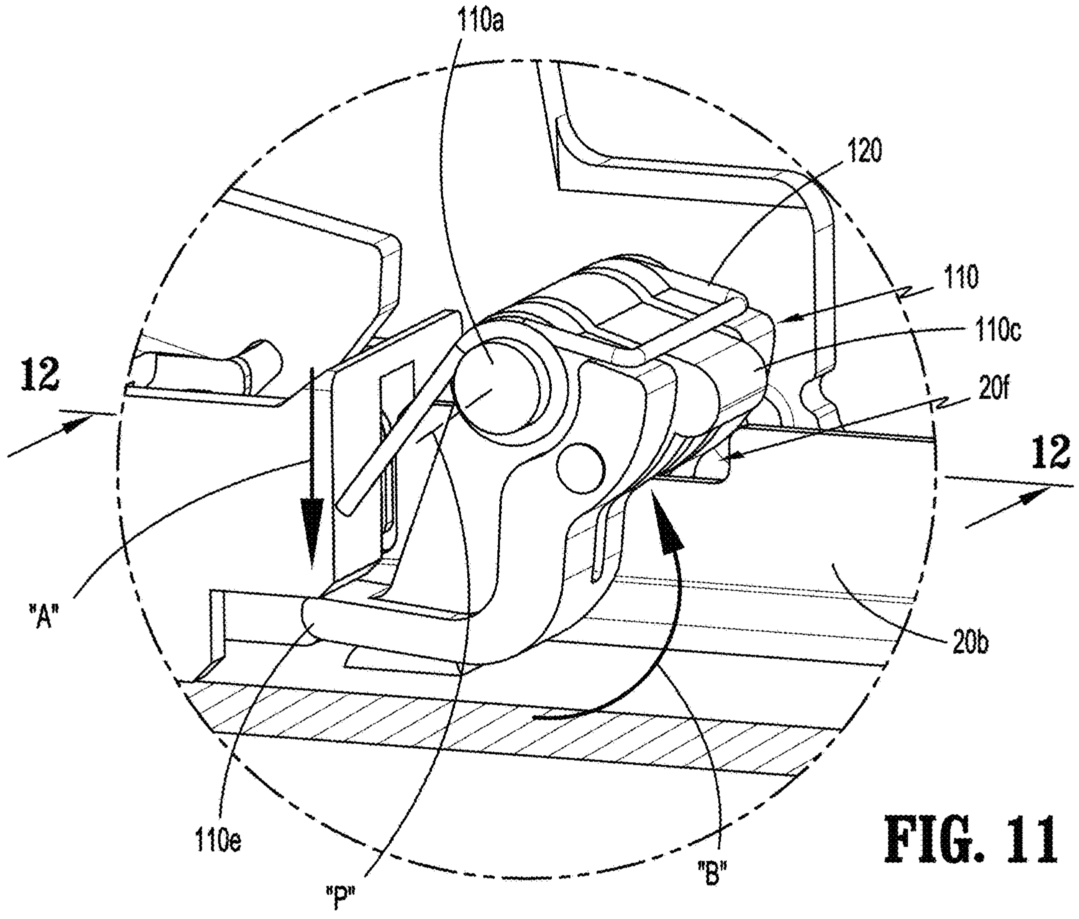
Figure 12:
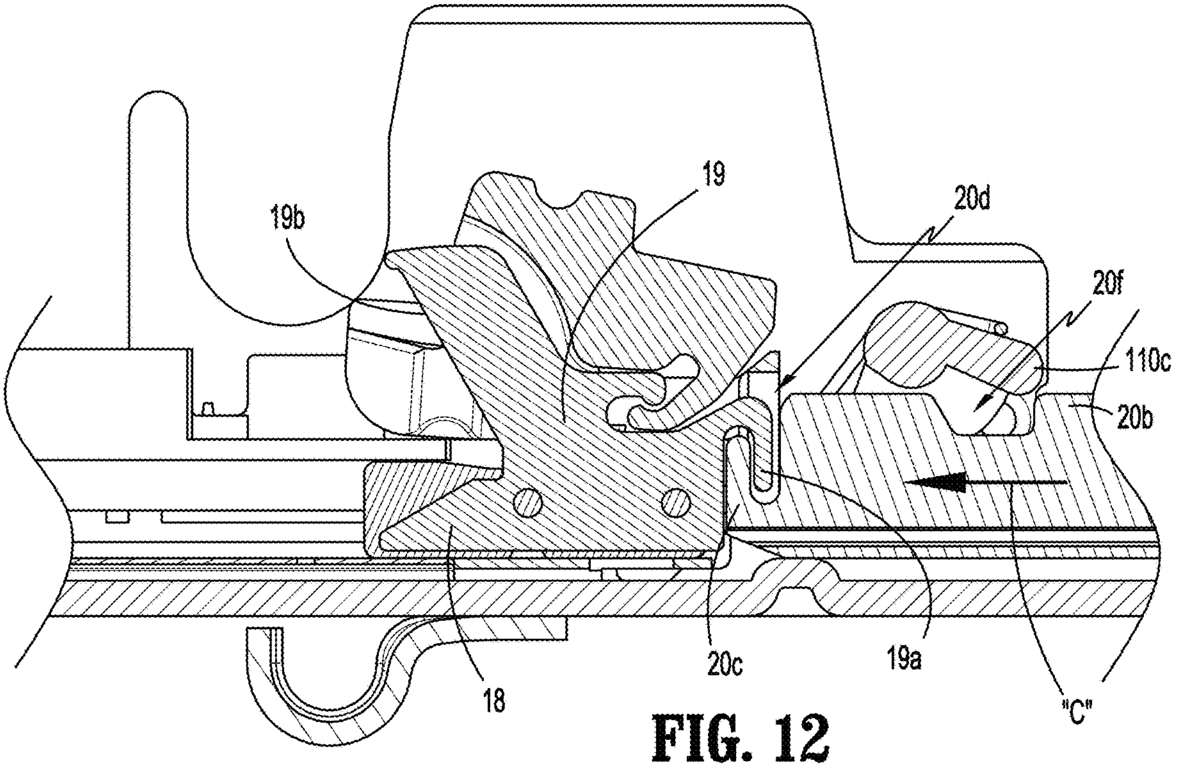

As seen in FIG. 11, when SULU 18 is received within elongated channel member 22 of cartridge receiving half-section 14, a proximal portion of SULU 18 engages distal toes 110*e* of lockout 110 and drives distal toes 110*e* downwardly, as indicated by arrow "A" so that lockout 110 pivots about shoulders 110*a*, namely, pivot axis "P," so that proximal tooth 110*c* of lockout 110 pivots out of recess 20*f* (e.g., counterclockwise), as indicated by arrow "B," into the unlocked position. In the unlocked position, a proximal finger 19*a* of a sled assembly 19 of SULU 18 is coupled to distal finger 20*c* of push plate 20*b* via finger recess 20*d* of push plate 20*b*. And in the unlocked position, firing assembly 20 can be advanced distally, as indicated by arrow "C" so that push plate 20*b* can translate through push plate passage 110*b* (FIG. 7) of lockout 110 and advance sled assembly 19 of SULU 18 distally through SULU 18 for firing staples from SULU 18 and cutting tissue with a knife 19*b* of sled assembly 19 as sled assembly 19 translates distally.

To remove SULU 18, firing assembly 20 to drawn proximally to an initial or proximal position in which proximal tooth 110*c* of lockout 110 is aligned with lockout recess 20*f*. SULU 18 can then be removed. As SULU 18 is removed, spring 120 of lockout assembly 100 causes lockout 110 to pivot in a clockwise direction about pivot axis "P" so that proximal tooth 110*c* is received within lockout recess 20*f* of push plate 20*b*, locking firing assembly 20 in the locked position.

Persons skilled in the art will understand that the structures and methods specifically described herein and illustrated in the accompanying figures are non-limiting exemplary embodiments, and that the description, disclosure, and figures should be construed merely as exemplary of particular aspects. It is to be understood, therefore, that this disclosure is not limited to the precise aspects described, and that various other changes and modifications may be effected by one skilled in the art without departing from the scope or spirit of this disclosure. Additionally, it is envisioned that the elements and features illustrated or described in connection with one exemplary aspect may be combined with the elements and features of another without departing from the scope of this disclosure, and that such modifications and variations are also intended to be included within the scope of this disclosure. Indeed, any combination of any of the disclosed elements and features is within the scope of this disclosure. Accordingly, the subject matter of this disclosure is not to be limited by what has been particularly shown and described.

What is claimed is:

1. A surgical fastener applying apparatus comprising:
an anvil half-section;
a cartridge receiving half-section defining an elongated channel member configured to receive a single use loading unit (SULU);
a firing assembly including a push plate; and
a lockout assembly having a lockout pivotally mounted in the elongated channel member,
wherein the lockout includes a distal toe positioned to contact the SULU, such that insertion of the SULU pivots the lockout from a locked position engaging the push plate to an unlocked position disengaged from the push plate, and wherein the SULU includes a proximal portion configured to engage the distal toe of the lockout.

2. The apparatus of claim 1, wherein the lockout includes a proximal tooth received within a recess of the push plate in the locked position.

3. The apparatus of claim 2, wherein the proximal tooth prevents distal translation of the push plate when received in the recess.

4. The apparatus of claim 1, wherein the lockout defines a push plate passage through which the push plate translates in the unlocked position.

5. The apparatus of claim 1, wherein the lockout includes arms that engage a stopper extending from the elongated channel member to limit clockwise rotation.

6. The apparatus of claim 1, wherein the lockout is biased into the locked position by a spring.

7. The apparatus of claim 1, wherein the distal toe is integrally formed with the lockout.

8. The apparatus of claim 1, wherein the lockout is pivotable about a pivot axis transverse to a longitudinal axis of the elongated channel member.

9. The apparatus of claim 1, wherein the firing assembly is configured to drive a sled assembly of the SULU when the lockout is in the unlocked position.

10. A surgical fastener applying apparatus comprising:
an anvil half-section;
a cartridge receiving half-section defining an elongated channel member configured to receive a single use loading unit (SULU);
a firing assembly including a push plate; and
a lockout assembly including a lockout pivotally mounted in the elongated channel member,
wherein the elongated channel member includes a guide nub extending upwardly from a base, the guide nub vertically constraining the push plate when the lockout is in a locked position.

11. The apparatus of claim 10, wherein the guide nub maintains the push plate at a predetermined distance above a base plane of the elongated channel member.

12. The apparatus of claim 10, wherein the lockout includes a proximal tooth received within a recess of the push plate in the locked position.

13. The apparatus of claim 12, wherein the push plate is vertically constrained between the guide nub and the proximal tooth.

14. The apparatus of claim 10, wherein the lockout defines a push plate passage through which the push plate translates in an unlocked position.

15. The apparatus of claim 10, wherein the lockout includes arms that engage a stopper extending from the elongated channel member to limit clockwise rotation.

16. The apparatus of claim 10, wherein the lockout is biased into the locked position by a spring.

17. The apparatus of claim 10, wherein the guide nub is integrally formed with the base of the elongated channel member.

18. The apparatus of claim 10, wherein the guide nub prevents vertical displacement of the push plate during attempted firing when the SULU is not present.

19. A surgical fastener applying apparatus comprising:

an anvil half-section;

a cartridge receiving half-section defining an elongated channel member configured to receive a single use loading unit (SULU);

a firing assembly including a push plate; and a lockout assembly supported in the elongated channel member and including a lockout pivotally mounted in the elongated channel member, wherein the lockout is biased into a locked position by a spring, wherein removal of the SULU causes the lockout to pivot into the locked position such that the lockout engages the push plate to prevent distal movement of the push plate, wherein the lockout includes a distal toe positioned to contact the SULU, and wherein the SULU includes a proximal portion configured to engage the distal toe of the lockout.

* * * * *